United States Patent [19]

Haynes

[11] Patent Number: 5,637,625
[45] Date of Patent: Jun. 10, 1997

[54] PROPOFOL MICRODROPLET FORMULATIONS

[75] Inventor: Duncan H. Haynes, Miami, Fla.

[73] Assignee: Research Triangle Pharmaceuticals Ltd., Durham, N.C.

[21] Appl. No.: 616,511

[22] Filed: Mar. 19, 1996

[51] Int. Cl.$^6$ .................................................. A61K 31/05
[52] U.S. Cl. ............................................................. 514/731
[58] Field of Search ............................ 514/731; 424/450, 424/490

[56] References Cited

U.S. PATENT DOCUMENTS

| | | | |
|---|---|---|---|
| 4,056,635 | 11/1977 | Glen et al. | 424/346 |
| 4,452,817 | 6/1984 | Glen et al. | 424/346 |
| 4,725,442 | 2/1988 | Haynes | 424/490 |
| 4,798,846 | 1/1989 | Glen et al. | 514/731 |

OTHER PUBLICATIONS

King et al Anesth Analg (1992); 74:246–9 pp. 246–249 "Lidocaine for the Prevention of Pain due to Injection of Pain Due to Injection of Propofol".

Freeman Anesth Analg (1992); 74:311–9 "A Technique for Reducing Pain Associates with Propofol Administration".

Eddleston et al Intensive Care Med (1991) 17:424–426 "The effect on serum lipid concentrations . . . propofol administration".

Ewart et al Anaesthesia, (1992), vol. 47, pp. 146–148 Forum "2% Propofol for Sedation . . . ".

Dewandre et al Anaesthesia, (1994), vol. 49, pp. 8–12 "A Comparison of the 2% and 1% . . . ".

Bennett et al Postoperative Infections Traced to Contaminated Propofol vol. 333 No. 3 pp. 147–154 "Postoperative Infections . . . " (1994).

Smith et al Anesthesiology, vol. 81, No. 4, (Oct. 1994) "Propofol An Update on its Clinical Use".

*Primary Examiner*—Raymond Henley, III
*Attorney, Agent, or Firm*—Nixon & Vanderhye

[57] ABSTRACT

Formulations of phospholipid-coated microdroplets of propofol devoid of fats and triglycerides provide chronic sedation over extended periods of time without fat overload. Being free of nutrients that support bacterial growth, these microdroplet formulations are bacteriosatic and bactericidal (e.g. self-sterilizing) and thus have extended shelf life.

7 Claims, 2 Drawing Sheets

PROPOFOL MICRODROPLET FORMULATIONS

This invention relates to pharmaceutical formulations of the intravenous anesthetic propofol.

BACKGROUND OF THE INVENTION

The present invention provides formulations of the intravenous anesthetic drug propofol (2,6-diisopropylphenol) as a phospholipid-coated microdroplet substantially completely devoid of fats or triglycerides. Such formulations offer advantages for chronic use in sedation, where fat (triglyceride) overload is presently an important clinical consideration. The formulation of the present invention is also shown to be bacteriostatic and bactericidal.

Propofol is a hydrophobic, water-insoluble oil. It has been incorporated in a vegetable oil emulsion to overcome the problem of its low water solubility and enable its use as an intravenous anesthetic agent. The clinically-available product (PDR, 1995) is a sterile, nonpyrogenic emulsion containing 1% (w/v) propofol in a white, 10% (w/v) soybean oil in water emulsion stabilized by 1.2% (w/v) lecithin (Diprivan®). Sterile pharmaceutical compositions of propofol and their use in inducing anesthesia are described in U.S. Pat. Nos. 4,056,635; 4,452,817 and 4,798,846 all to Glen and James. The propofol/soybean oil emulsion has gained widespread use for induction and/or maintenance of anesthesia, for maintenance of monitored anesthesia care and for sedation in the Intensive Care Unit (ICU). It produces rapid onset anesthesia with a short recovery time Two problems associated with the use of vegetable oil in the commercial 1% propofol/10% soybean oil emulsion are: (1) hyperlipidemia in patients undergoing long-term ICU sedation, and (2) the risk of bacterial contamination secondary to the high lipid content and lack of antimicrobial preservatives.

The present invention provides phospholipid-coated propofol microdroplet formulations (MD-Propofol) which allow propofol to be delivered at a higher "payload" on a weight per volume basis than the current clinically available product without soybean oil, or other fats or triglycerides.

The formulation of propofol for intravenous administration without using soybean oil, fats or triglycerides is an important feature of the present invention. Studies by Gottardis et at., 1989, De Soreruer, et al., 1990, Lindholm, 1992, and Eddieston and Shelly, 1991 have shown that triglyceride overload can become a significant problem when the 1% propofol/10% soybean oil emulsion is used as the sole sedative for long-term ICU sedation. Administration of the propofol/soybean oil emulsion elevates serum lipids in exactly the same way as does the Intralipid® product on which it is based. It has been reported that if propofol/soybean oil emulsion is given in the ICU for sedation together with IV hyperalimentation, the lipid load may exceed the patient's capacity to clear the IV fats, resulting in "fat overload syndrome". The associated hyperlipidemia can result in increased bilirubin levels, "fatty liver", liver damage and other adverse consequences. It is further noted that lipid tolerance may be reduced in critically ill patients secondary to altered metabolic enzyme systems. Experimentation with a 2% propofol emulsion which delivers less fat per unit propofol has been reported (Ewart et al, 1992; Dewandre et al 1994).

The formulation of propofol for intravenous administration free of the risk of bacterial growth is a second important feature of the present invention. The commercially-available product will grow bacteria and presents a risk of bacterial contamination as the result of its high triglyceride content and lack of antimicrobial preservatives (Arduino et al., 1991; Sosis & Braverman, 1993; PDR, 1995). Phospholipid-coated propofol microdroplets of the present invention do not support the growth of bacteria, and are, in fact, bactericidal.

The phospholipid-coated microdroplets at about 0.1 μm diameter droplet of drug in the oil state, coated with a stabilizing monolayer of phospholipid are described in my earlier patents U.S. Pat. Nos. 4,622,219 and 4,725,442, the disclosures of which are hereby incorporated by reference. Microdroplet formulations have been made for many compounds including methoxyflurane, isoflurane and Vitamin E. The present invention provides a formulation of microdroplet propofol which allows the administration of propofol without the fat.

BRIEF DESCRIPTION OF THE DRAWINGS

The invention is illustrated in the appended drawings.

DESCRIPTION OF THE PREFERRED EMBODIMENTS

Figure 1:
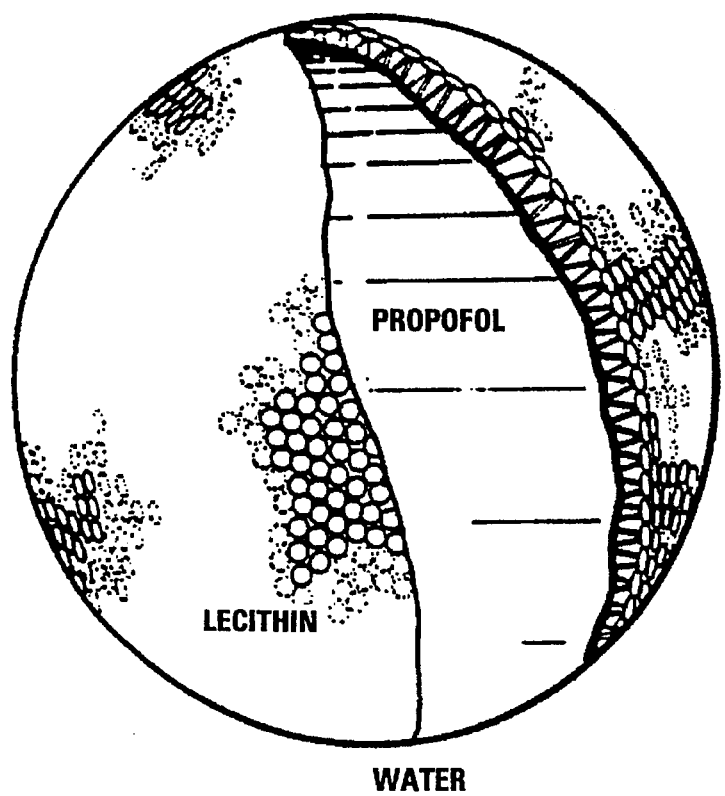
FIG. 1 is a schematic representation of the lecithin-coated propofol microdroplet.

The coating material of the propofol microdroplet can be chosen from the lipids described in my U.S. Pat. No. 4,725,442 (incorportated herein by reference) columns 5–7, particularly the phospholipids described in Class A, B and C. Additionally, the microdroplet can be coated by certain mono-glycerides capable of forming oriented monolayers and bilayers in the presence of decane (Benz et al. Biochim. Biophys. Acta 394:323–334, 1975). Examples of useful mono-glycerides include, but are not limited to, the following:

1-monopalmitoyl-(rac)-glycerol (Monopalmitin)

1-monocaprylol-(rac)-glycerol (Monocaprylin)

1-monooleoyl-(rac)-glycerol (C18:1, cis-9) (Monoolein)

1-monostearyl-(rac)-glycerol (Monostearin)

Phosphatidylcholine (lecithin) is the most useful example. Egg Phospholipids, P123, from Pfanstiehl Laboratories, Waukegan, Ill. is a pharmaceutical grade of lecithin, containing some phosphatidylethanolamine and cholesterol. Additionally, stearoyl-, dimyfistoyl- and dipalmitoyl-lecithin are available in pharmaceutical grade from Avanti Polar Lipids, Alabaster, Ala. and can be used after testing shows that the resultant product has the requisite physical stability over a range of temperatures.

Preparation of propofol microdroplets requires intense mechanical agitation or high sheer. The preferred method of preparing propofol microdroplets of the invention on the laboratory scale is sonication with a probe sonicator. For industrial scale production, Microfluidization® (Microfluidics Corp., Newton, Mass. 02164) is preferred. The process creates high shear by collision of opposing jets of liquid. The apparatus is described by Mayhew et al. in Biochim. Biophys. Acta 775:169–174, 1984. Alternative industrial scalable processors include but are not limited to the Gaulin and Rannie Homogenizers (APV Gaulin/Rannie Homogenizers, St. Paul, Minn.).

The present invention is further described with reference to the following examples. In these examples a single aqueous glucose/phosphate buffer solution, consisting of 300 mM glucose, 2 mM $Na_2HPO_4$ with pH adjusted to 7.0 with HCl, was used as aqueous vehicle for the microdroplet propofol formulations, for dilutions of the preparation and for in vitro experimentation.

Propofol concentrations in the preparations and in vitro experiments were determined by HPLC assay of methanol extracts using a Beckman 334 Gradient Liquid Chromatograph system with the following parameters: Mobile phase, methanol/water 65%/35% (v/v); flow rate, 1.5 mL/min; UV Detector 271 nm; Whatman Partisil 5 ODS-3 column, 25 cm; injection volume, 50 µL.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers (µm=$10^{-6}$ meters), nanometers (nm=$10^{-9}$ meters) or Angstrom units (=0.1 nm). Volumes are given in liters (L), milliliters (mL=$10^{-3}$ L) and microliters (µL=$10^{-6}$ L). Dilutions are by volume. All temperatures are reported in degrees Celsius. The compositions of the invention can comprise, consist essentially of or consist of the materials set forth and the process or method can comprise, consist essentially of or consist of the steps set forth with such materials.

EXAMPLE 1

(Propofol Microdroplet Preparation)

Lecithin (0.328 gm, Egg Phospholipids, P123, Pfanstiehl Laboratories, Waukegan, Ill.), glucose/phosphate buffer (9.0 mL) and 2,6-Diisoproplyphenol (1.0 mL, propofol, 97%, Aldrich Chemical Co., St. Louis, Mo.) were placed in a glass test tube which was suspended in a beaker of water at room temperature, and was sonicated by a Heat Systems-Ultrasonics (Plainview, N.Y.) Sonifier® Cell Disruptor Model W185D with microtip. Since propofol in the pure oily state is an irritant, gloves were worn during the initial handling and sonication was performed in a fume hood. The sonication was at 60 watts for a total sonication time of 10 minutes, with 2 min. on/2 min. off cycles to minimize heating to the sample. The pH after sonication was adjusted to 7.0 using NaOH. This procedure yielded lecithin-coated propofol microdroplets. The preparation is a homogeneous off-white suspension.

HPLC analysis established a propofol concentration of 68 mg/ml (6.8% w/v) for the sample.

Particle size analysis was performed utilizing a Coulter Model N4MD Sub Micron Particle Analyzer (Coulter Electronics, Hialeah, Fla.). The sample was diluted into propofol-saturated glucose/phosphate buffer to minimize net release of propofol from the microdroplets. The analysis showed unimodel size distribution with an average diameter of 164±54 (SD) nm.

The sample was also examined by light microscopy using a Zeiss Fluorescent Microscope in transmission mode and was observed as a tightly-packed suspension of 0.1–0.2 µm particles. With dilution in propofol-saturated buffer, the propofol microdroplets were observed as independent 0.1–0.2 µm particles undergoing Brownian motion.

The preparation was stored at room temperature. During an 18-month period subsequent to the experimentation, the preparation did not exhibit any settling or "creaming", and did change color or consistency. Importantly, no sign of bacterial or fungal growth was observed.

EXAMPLE 2

(Efficacy for General Anesthesia in Rats)

The lecithin-coated microdroplet propofol formulation of Example 1 (MD-Propofol) was compared with the commercial Diprivan® product for efficacy of inducing anesthesia in laboratory rats. Diprivan® (Diprivan® 1%, Injection propofol, 10 mg/ml, Emulsion for I.V. Administration, Stuart Pharmaceuticals) was purchased. It is described by the manufacturer as a sterile, nonpyrogenic emulsion containing 10 mg/mL propofol, 100 mg/ml soybean oil, 12 mg/mL lecithin in an aqueous vehicle. It was maintained at room temperature as described by the manufacturer. Samples were taken using aseptic technique.

Lecithin-coated propofol microdroplets containing 6.8% propofol and Diprivan® were injected into the tail veins of 150 gram female CD laboratory rats (Charles River Laboratories, Wilmington, Mass.) restrained in a Decapicone® (Braintree Scientific, Braintree, Mass.). The volumes of 6.8% (w/v) microdroplet propofol injected were 10, 20, 30 or 50 µL. The injections were accomplished in 2–3 seconds. Volumes of 1% Diprivan® injections were 100, 200, 300 or 500 µL. The injections were accomplished in 5–15 seconds. The animals were observed during the injections, and the time required for loss of consciousness ("time to unconsciousness") was recorded. Then the animals were removed from the Decapicone® and placed on their sides and were tested for startle response to a loud clap. A flinch response indicates shallow anesthesia; lack of response indicates deep anesthesia. The time to regain startle response ("time to startle response") was recorded. The time to recover the righting response, indicated by spontaneous attempt to stand, was also measured. Finally, the elapsed time for the rat to return to baseline physical activity was taken as the "time to full recovery" from the effects of the drug.

Tables 1 and 2 present dose-response data for lecithin-coated microdroplet propofol and Diprivan®, respectively, in laboratory rats. The tables present, as a function of dose, the average values for (a) the time required for the animal to be rendered unconscious, (b) the time elapsing before the animals regained startle response to a loud clap, (c) time elapsing before the animals regain fighting response, and (d) the time required for full recovery. The tables also present mortality data.

Figure 2:
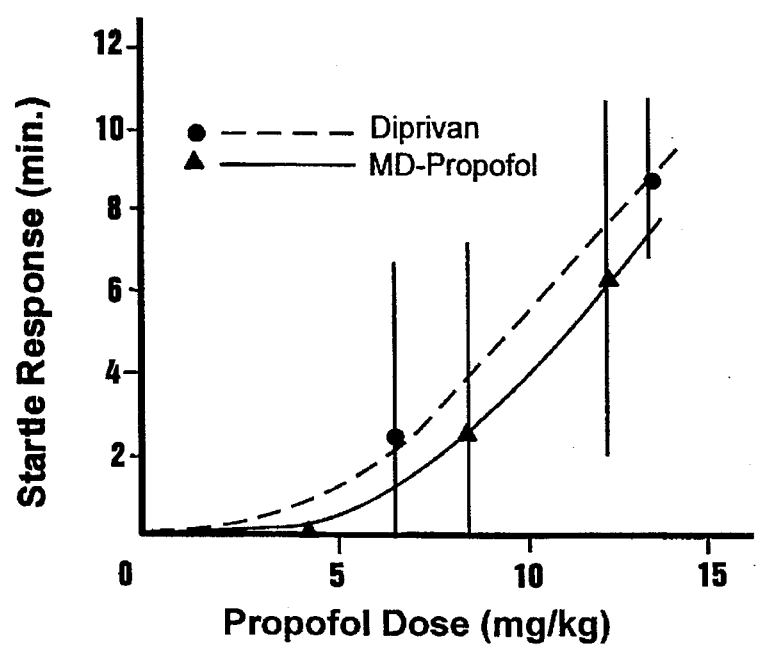
FIG. 2 is a graph illustrating the duration of suppression of startle response as a function of propofol dose for microdroplet propofol of the present invention as compared with the conventional propofol/soybean oil emulsion.
Figure 3:
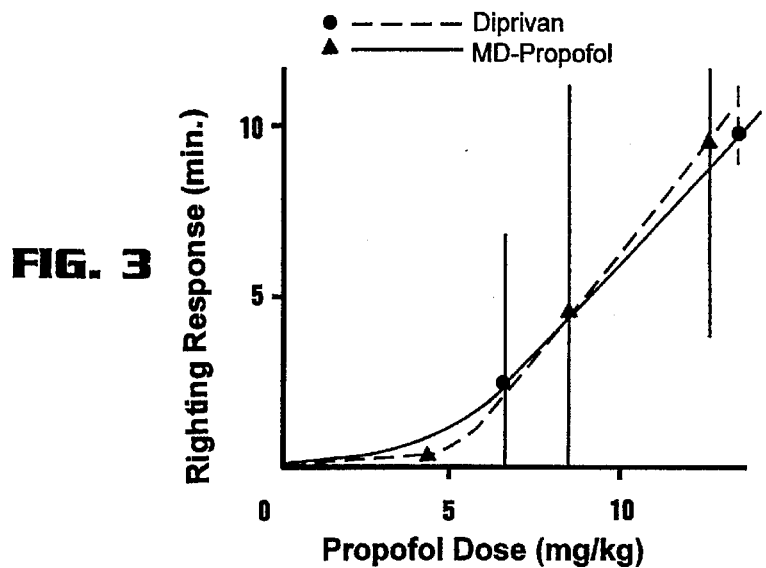
FIG. 3 is a graph illustrating the duration of suppression of righting response as a function of propofol dose for microdroplet propofol of the present invention as compared with the conventional propofol/soybean oil emulsion.
Figure 4:
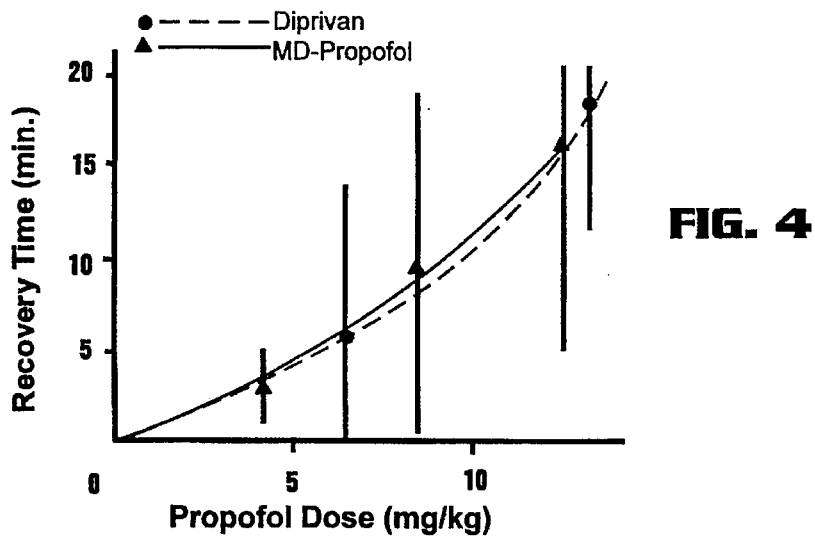
FIG. 4 is a graph illustrating the recovery time as a function of propofol dose for microdroplet propofol of the present invention as compared with the conventional propofol/soybean oil emulsion.

FIGS. 2–4 show that MD-propofol and Diprivan® are have equivalent dose-response relationships for the four parameters.

FIG. 2 compares graphically the dose-response data of MD-Propofol and propofol/soybean oil emulsion for the duration of the startle response. The dose-response curves for the two agents are identical, within the experimental variation. The startle response represents the deepest degree of anesthesia measurable in a non-surgical study. Student's test showed no significant difference (p=0.85) in the startle response durations of MD-Propofol vs. Diprivan® at the 12.6–13.3 mg/kg dose.

FIGS. 3 and 4 compare for MD-Propofol and Diprivan® times to the return of righting response and full recovery, respectively. The dose-response curves for the two agents overlapped and Student's t-test indicate no significant response differences (p=0.50 and 0.42, respectively) at the 12.6–13.3 mg/kg dose.

Propofol doses at 20–21 mg/kg produced significant mortality, tabulated in Tables 1 and 2. The limited number of observations does not provide a statistical basis for distinguishing mortality rates between the two groups.

Since microdroplet propofol was 6.8 times as concentrated as the conventional propofol/soybean oil emulsion, and since it was injected in shorter times, the effects of diluting each formulation were investigated. Table 1 shows that administering the 12.6 mg/kg dose of microdroplet propofol in a 4-fold larger volume did not have a significant effect on any of the four measures of anesthetic action. Similarly, 4-fold dilution of the 20 mg/kg dose of propofol/soybean oil emulsion is without significant effect.

Miami, Fla.) in 10×75 mm borosilicate glass test tubes with vortex mixing, and were allowed to react for approx. 30 sec. or 10 minutes in absence of agitation. Then 210–250 µL aliquots were transferred into tared polyethylene centrifuge tubes and were centrifuged in a Coleman Microfuge for approximately 3 minutes. Propofol microdroplets migrated to the air-water interface. Propofol has a density of 0.955. Similarly, propofol/soybean oil emulsion migrated to the air-water interface. Soybean oil has a density of 0.916–0.922.

The tubes were frozen, weighed, and were cut into two sections which were weighed. Then the contents were extracted for propofol using acidified methanol, which precipitated the plasma proteins, allowing them to be removed by further centrifugation. As a control for this procedure, human plasma was also spiked with known quantifies of propofol and was assayed. This verified an extraction efficiency of 100% (103±35%).

Table 3 gives the percentage of propofol released to human plasma after 29–31 sec and 10 min. MD-propofol and Diprivan® achieve a maximal release corresponding to 93% and 97% (respectively) of their propofol within 32–34 sec. The difference between the two preparations was not significant.

TABLE 1

Microdroplet-propofol dose-response in rats.

| MD-Propofol dose(mg/kg) | Time to (min) Unsconsciousness | Time to Startle Response (min) | Time to Righting Response (min) | Time to Full Recovery (min) | Mortality/n |
|---|---|---|---|---|---|
| 4.2 | NA | 0.00 | 0.00 | 3.0 ± 2.0 | 1/4 |
| 8.4 | <1.0 | 2.5 ± 5.0 | 4.7 ± 7.1 | 9.8 ± 9.2 | 0/4 |
| 12.6 | <1.0 | 6.6 ± 4.5 | 9.9 ± 5.9 | 16.1 ± 11.0 | 0/4 |
| 12.6* | <1.0 | 3.7 ± 4.7 | 4.5 ± 4.5 | 9.7 ± 8.8 | 0/5 |
| 21.0 | <1.0 | ** | ** | ** | 3/5 |

*Diluted 4-fold with 300 mM glucose phosphate buffered solution at pH 7.0
**Two rats were saved,by manual cardiac chest compression
NA = Never Achieved

TABLE 2

Diprivan ® dose-responses in laboratory rats.

| Diprivan ® dose (mg/kg) | Time to(min) Unconsciousness | Time to Startle Response(min) | Time to Righting Response (min) | Time to Full Recovery (min) | Mortality/n |
|---|---|---|---|---|---|
| 6.7 | <1.0 | 2.5 ± 4.3 | 2.5 ± 4.3 | 6.0 ± 7.9 | 0/3 |
| 13.3 | <1.0 | 8.8 ± 2.6 | 10.1 ± 1.1 | 18.4 ± 6.3 | 0/5 |
| 20.0 | <1.0 | 12.3 ± 5.3 | 15.0 ± 5.6 | 27.3 ± 6.3 | 1/4 |
| 20.0* | <1.0 | 14.0 ± 4.6 | 16.7 ± 2.5 | 25.3 ± 5.0 | 2/3 |
| 33.3 | <1.0 | ** | ** | ** | 4/5 |

*Diluted 4-fold with 300 mM glucose phosphate solution buffered at pH 7.00
**Single survivor believed to be due to subcutaneous extravastion upon I.V. injection

EXAMPLE 3

(Release of Propofol into Human Plasma)

This Example shows that both MD-Propofol and Diprivan® can release their propofol to human plasma in 30 seconds or less.

Aliquots of 6.8% microdroplet propofol or (1%) propofol/(10%) soybean oil emulsion (Diprivan®) were diluted 200-fold into human plasma (Continental Blood Services,

TABLE 3

Comparison of Dissolution Percentages in Propofol Microdroplets vs. Diprivan® in Human Plasma

| Preparation | Time After Dilution | % Propofol Dissolved | % Propofol Undissolved |
|---|---|---|---|
| MD-Propofol | 34 ± 3 seconds | 92.7 ± 8.9 | 7.3 ± 8.9 |
| Diprivan® | 32 ± 5 seconds | 97.4 ± 5.7 | 2.6 ± 5.7 |
| MD-Propofol | 10 minutes | 93.6 ± 7.8 | 6.4 ± 7.8 |
| Diprivan® | 10 minutes | 99.5 ± 1.3 | 0.5 ± 1.3 |

MD-Propofol was diluted 200x to 0.340 mg/ml;
Diprivan® was diluted 200x to 0.050 mg/ml

EXAMPLE 4

(Release from MD-Propofol Monitored by Light Scattering)

The rate of shrinkage of propofol microdroplets accompanying propofol release was measured by light scattering. As propofol microdroplets lose their highly refractive propofol core and convert into liposomes or membrane fragments, their 90° light scattering efficiency is decreased. The kinetics of shrinkage of MD-Propofol were monitored using Perkin-Elmer Model MPF-3L Fluorescence Spectrophotometer in light scattering mode and equipped with a magnetic stirrer. The reaction took place in a clear 4-sided acrylic cuvette containing a Teflon-coated magnetic stirrer and filled with 2.0 mL of a 5% solution of bovine serum albumin (Sigma) as propofol acceptor or glucose/phosphate buffer as a control. Human plasma could not be used as a propofol acceptor since its intrinsic light scattering roughly equaled that of the propofol microdroplets.

Figure 5:
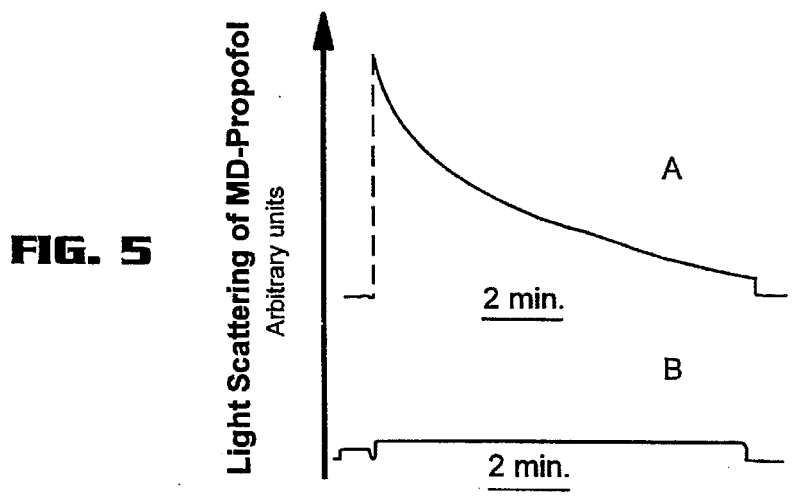
FIG. 5 is a graph illustrating the kinetics of shrinkage of the lecithin-coated propofol microdroplet of the present invention measured by decrease in light scattering after 200-fold dilution in which Curve A is dilution into glucose/phosphate buffer and Curve B is dilution into 5% bovine serum albumin.

FIG. 5, curve A is a typical experiment showing the kinetics of decrease of light scattering when propofol microdroplets (6.8% w/v) of Example 1 are diluted 200-fold into a stirred glucose/phosphate buffer. Introduction of the microdroplets causes an instantaneous rise in light scattering. A decrease is observed over several minutes as the microdroplets release propofol. The earliest signal detected was back-extrapolated to zero time to obtain its maximal value at the time of dilution.

In Curve B of FIG. 4, the experiment was repeated in 5% bovine serum albumin. The figure shows that the earliest light scattering signal detected is only a small fraction of that observed in glucose/phosphate buffer and that the subsequent trace is flat. The differences in refractive indices of the media cannot account for the loss of light scattering. Thus propofol release to the BAS medium was achieved within the two second mixing time of the experiment.

By repeating the above experiment at a higher sensitivity and chart speed, we could observe the last 1% of the light scattering decrease and determine a half-time of less than 1 sec. The experiment was repeated several times with similar results. The observable initial amplitude in the BSA experiment is only 4% of that in the glucose buffer experiment. Conservatively estimated, the propofol release to BSA is at least 96% complete within 2 sec.

The light scattering experiments showed that microdroplet propofol can release at least 94% of its propofol to the stirred glucose buffer. Several repetitions gave a half-time of 91±25 (SD) sec. In these experiments, continuous stirring was necessary for maximal rate of release of propofol from the microdroplets.

With microdroplet propofol, the time required for complete release to BSA is less than 2 sec. Rapid release to plasma proteins during such short times is consistent with monomeric propofol entering the brain on its first pass, as can be deduced from the <1 minute time to unconsciousness in the experiments of Example 2.

It was not practical to study Diprivan® release of propofol by the light scattering method. Diprivan® particles do not shrink appreciably since vegetable oil is their major constituent before and after maximal propofol release.

EXAMPLE 5

(Bacteriostatic and Bactericidal Activity of MD-Propofol)

The microdroplet formulation of Example 1 (6.8% w/v propofol) was tested for bacteriostatic and bactericidal activity following the guidelines set forth United States Pharmacopea 23, 1995, Section <71> Sterility Tests, pp. 1686–1689. Consecutive dilutions of E. Coli bacteria SRB strain were made from a stock growth suspension (LB Broth Base, Gibco BRL, Cat. #12780-052, Lot #10E0252B) into sterile water. Volumes of 0.1 mL of the dilutions were added to 5 ml volumes of 9:1 mixtures of sterile growth medium, yielding a propofol concentration of 0.67% (w/v). A 0.1 ml volume of each bacteria dilution was also plated on growth agar to determine the number of bacteria added to each of the test cultures. After 7 days of incubation at 37° C., the samples of the test cultures were plated onto growth agar to check for viable bacteria, and the plated bacteria cultures were counted.

The above experiments on MD-Propofol diluted to 0.67% (w/v) gave the following results: MD-Propofol was bactericidal at bacteria concentrations of 200 or less colony forming units per mL. MD-Propofol was bacteriostatic at bacteria concentrations of 500 to 1,000 colony forming units per mL.

Accordingly, the microdroplet propofol formulations of the present invention being free of fats and triglycerides are self-stabilizing and afford considerably longer shelf life and the opportunity for less demanding manufacturing and packaging conditions.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

ADDITIONAL LITERATURE CITED

Arduino, M. J. (1991)Infect. Control Hosp. Epidemiology 12(9):535–549

Eddleston, J. M, Shelly, M. P. (1991) Intensive Care Med. 17(7):424–426

Ewart, M. C., et al. (192)Anesthesia 47(2):146–148

De Sommer, M. R. et al. (1990) Acta Anaesthesia Belgica 41(1):8–12

Dewandre, J. et al. (1994) Anaesthesia 49(1):8–12

Gottardis, M. et al. (1989) British J. Anaesthesia 62:393–396

Lindholm, M. (1992) Minerva Anaesthesiology 58(10):875–879

PDR (1995) entry, Smart Pharmaceuticals, Wilmington, Del., in Physician's Desk Reference, Medical Economics, Montvale, N.J., pp. 2436–2441

Sosis, M. B., Braverman, B. (1993) Anesthes. Analges. 77(4):766–768

What is claimed is:

1. A microdroplet of about 200 Angstrom up to one micron in diameter consisting essentially of a sphere of propofol surrounded by a stabilizing layer of a phospholipid and devoid of oils capable of supporting bacterial growth.

2. A sterile, pyrogen free, injectable pharmaceutical composition consisting essentially of the microdroplets of claim 1, together with a pharmaceutically acceptable injectable vehicle.

3. The injectable pharmaceutical composition of claim 2, in which the injectable vehicle is an isotonic solution.

4. The microdroplet of claim 1, having a diameter of up to 10,000 Angstroms.

5. An anti-microbial pharmaceutical composition consisting essentially of:

(1) microdroplets of from about 200 Angstroms to one micron in diameter produced by sonification, homogenization, microfluidization or other processes involving high shear and consisting of a propofol core stabilized against coalescence and surrounded by a phospholipid membrane layer, wherein the ratio of the volume of propofol to the weight of the phospholipid membrane layer is at least 1.0 ml/g the composition contains at least 3% w/v propofol and is devoid of fats and triglycerides; and (2) a pharmaceutically acceptable injectable carrier.

6. A bactericidal pharmaceutical composition consisting essentially of:

(1) microdroplets of from about 200 Angstroms to one micron in diameter produced by sonification, homogenization, microfluidization or other processes involving high shear and consisting of a propofol core stabilized against coalescence and surrounded by a phospholipid membrane layer, wherein the ratio of the volume of propofol to the weight of the phospholipid membrane layer is at least 1.0 ml/g the composition contains at least 3% w/v propofol and is devoid of fats and triglycerides; and (2) a pharmaceutically acceptable injectable carrier.

7. A sterile, injectable pharmaceutical composition consisting essentially of:

(1) microdroplets of from about 200 Angstroms to one micron in diameter produced by sonification, homogenization, microfluidization or other processes involving high shear and consisting of a propofol core stabilized against coalescence and surrounded by a phospholipid membrane layer, wherein the ratio of the volume of propofol to the weight of the phospholipid membrane layer is at least 1.0 ml/g the composition contains at least 3% w/v propofol and is devoid of fats and triglycerides; and (2) a pharmaceutically acceptable injectable carrier.

* * * * *